(12) United States Patent
Morita

(10) Patent No.: US 9,121,842 B2
(45) Date of Patent: Sep. 1, 2015

(54) METHOD FOR ASSESSING CONDITION OF FIBERS

(75) Inventor: Naohiro Morita, Nishinomiya (JP)

(73) Assignee: The Procter & Gamble Company, Cincinnati, OH (US)

(*) Notice: Subject to any disclaimer, the term of this patent is extended or adjusted under 35 U.S.C. 154(b) by 200 days.

(21) Appl. No.: 13/560,373

(22) Filed: Jul. 27, 2012

(65) Prior Publication Data
US 2013/0025360 A1 Jan. 31, 2013

Related U.S. Application Data

(60) Provisional application No. 61/512,762, filed on Jul. 28, 2011.

(51) Int. Cl.
  G01D 7/02 (2006.01)
  G01N 33/483 (2006.01)
  A61B 5/00 (2006.01)

(52) U.S. Cl.
  CPC ............ *G01N 33/4833* (2013.01); *A61B 5/448* (2013.01)

(58) Field of Classification Search
  USPC .................................................... 73/159, 160
  See application file for complete search history.

(56) References Cited

U.S. PATENT DOCUMENTS 3,459,197 A * 8/1969 Wilson .......................... 132/148
3,490,585 A * 1/1970 Gooding et al. ................. 209/5
3,921,443 A * 11/1975 Yates ............................... 73/817
6,736,017 B2 * 5/2004 Mansky ................... 73/862.046
7,508,508 B2 * 3/2009 Grossinger et al. ........... 356/328
2003/0041663 A1 * 3/2003 Kossuth et al. ................. 73/159

FOREIGN PATENT DOCUMENTS

| CA | 2567712 | 5/2007 |
| JP | 2005-513029 | 5/2005 |
| JP | 2007-532925 | 10/2005 |
| JP | 2010-276558 | 12/2010 |
| JP | 2014-523040 | 1/2013 |

OTHER PUBLICATIONS

P. Quevauviller :"Certified reference material (CRM 397) for the quality control of trace element analysis of human hair".*
P.Quevauviller: "Certified referencematerial (CRM 397) for the quality control of trace element analysis of human hair", Fresenius J Anal Chem. vol. 343. Dec. 1, 1992 pp. 335-338.
Yuen C W M et al: "Evaluation of Keratin Fibre Damages", Fibers and Polymers. Korean Fiber Society.Seoul, KR vol. 8, No. 4, Jan. 1, 2007 pp. 414-420.
International Search Report PCT/US2012/048456; Mailing Date Nov. 2, 2012; 13 pages.

* cited by examiner

*Primary Examiner* — Hezron E Williams
*Assistant Examiner* — Xin Zhong
(74) *Attorney, Agent, or Firm* — Linda M. Sivik

(57) ABSTRACT

Disclosed herein is a method for assessing damages of keratin fibers using a mesh. Said methods are useful for assessing the degree of damages of keratin fibers and also to compare the damages of fibers of different origin, different portions of fibers and/or fibers treated with different cosmetic, chemical and/or mechanical treatments. Said methods are also useful for supporting advertising claims about the efficacy of a treatment.

9 Claims, 1 Drawing Sheet

METHOD FOR ASSESSING CONDITION OF FIBERS

CROSS REFERENCE TO RELATED APPLICATIONS

This application claims the benefit of U.S. Provisional Application No. 61/512,762 filed on Jul. 28, 2011.

FIELD OF THE INVENTION

In a first aspect, the present invention relates to a method for assessing conditions such as damages of fibers by using a mesh. In a second aspect, the present invention relates to a method for comparing conditions of different fiber samples using the above method.

BACKGROUND OF THE INVENTION

Keratin fibers, particularly human hair fibers, may be damaged over time. Damages may be caused by environmental factors, including air pollution, sun exposure, chlorine from water pool, and/or rain. Damages may also be caused by applying to the fibers grooming (cosmetic), chemical and/or mechanical treatments. When hair fibers are damaged, the hair fibers may have undesirable conditions of, for example, "fly-away hair", "split end", and/or color fade.

Assessing the condition including the degree of damages caused to hair fibers is of interest in order to understand the impact of various environmental factors as well as the impact of the cosmetic (grooming), chemical and mechanical treatments onto keratin fibers. Such assessment is also of interest in order to demonstrate the efficacy of treatments used for preventing and/or repairing hair damages. Several attempts for assessing hair damages, using different analytical methods, have already been reported.

However, these methods usually require many types of equipment and provide data to be interpreted by the skilled person, while being barely understandable for consumers and/or users. Thus, there still remain a need for providing methods to assess fiber conditions such as hair damages, especially such methods which are easy to conduct and/or easy to understand.

There may further exists a need for such method which allows a direct visualization of the degree of fiber condition such as hair damages

SUMMARY OF THE INVENTION

The present invention relates to a method for assessing a condition of fibers comprising the steps of:
providing at least one sample of fibers;
providing a mesh, wherein the mesh has holes which at least one fiber pass through;
placing said sample of fibers in contact with the mesh and allowing the fibers to pass through the mesh holes; and,
measuring the quantity of fibers passing through the mesh, of the sample;
assessing a condition of the sample based on the quantity of fibers.

The method allows assessing conditions of a sample of fibers, including degree of damage of hair fiber samples.

The present invention also relates to a method for assessing and comparing condition of different fibers comprising the steps of:
providing at least two different samples of fibers;
providing at least one mesh, wherein the mesh has holes which at least one fiber pass through;
placing said samples of fibers in contact with the mesh and allowing the fibers to pass through the mesh holes; and,
measuring the quantity of fibers passing through the mesh, of the samples;
assessing conditions of the samples based on the quantity of fibers;
comparing the condition of the samples.

The method allows assessing and comparing conditions of different fiber samples, including degree of damage of different hair fiber samples.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:
FIG. 1 is a photo comparing the quantity of fibers passing though mesh holes for Treatment step A vs. Treatment step B.

DETAILED DESCRIPTION OF THE INVENTION

Fiber Sample

The method of the invention comprises the step of providing at least one sample of fiber(s) (so-called "sample provision step"). As used herein, "fiber" means any fiber, and preferably that can be influenced by any of the cosmetic, chemical and/or mechanical treatments which are conducted separately from and/or during the method of the present invention. Said fiber is preferably a mammal hair, more preferably a human hair including a synthetic fibers made like a human hair (hereinafter "synthetic hair"). The origin of the human hair may be Caucasian, African, Asian, or any other origin. The hair fiber may be obtained from any part of the body, e.g. the legs, the arms, the torso, the face or the scalp. The hair fiber is preferably obtained from the scalp.

When the fibers are mammal hair, the damage assessment of the present invention can be done in vivo, using mammal hairs as hair samples without cutting. Alternatively, the assessment of the present invention can be done in-vitro.

A selected portion of fiber sample is used for the assessment method of the present invention. Any portion can be used, and fiber end tip portion may be preferred in view of understanding damage degree as well as understanding efficacy of treatments when used.

Said sample may comprise from about 100 fibers to about 300,000 fibers, preferably from about 500 fibers to about 150,000 fibers, more preferably from about 1,000 fibers to about 100,000 fibers. Said fibers may be bundled to each other such that the bundle has at least one free end. One sample usually comprises fibers of the same origin (e.g. from the same person and the same region of the body), and/or of the same portion (e.g. root end or tip end of hair fibers), and/or having been subjected to the same cosmetic, chemical and/or mechanical treatments. When providing at least two, preferably from two to four, more preferably two, different samples of keratin fiber(s), "different samples" means samples differing from each other by the origin of the fibers, the portion of the fibers and/or the treatment(s) applied to fibers.

The fibers may be of sufficient length for the damage assessment method of the present invention. The fibers have preferably a length of 1 cm to 50 cm, more preferably of 3 cm to 30 cm, still more preferably of 5 cm to 20 cm. When fibers are bundled to each other, it is preferred that the fibers have the above length from the point to be bundled.

Mesh

The method also comprises the step of preparing a mesh (so-called "mesh provision step") wherein the mesh has holes with a size such that at least one keratin fiber can pass through. Meshes, which are suitable for use in the present method, include any conventional meshes, as long as the meshes are composed by materials which are not broken by fibers when passing through.

It is preferred in the present invention that the hole of the mesh has a size of from about 1.1 times to about 20 times larger than the diameter of the fiber, more preferably from about 5 times to about 15 times larger than the diameter of the fiber, in view of accuracy of the assessment.

It is preferred in the present invention, especially when using hair fiber samples, that the hole of the mesh has a size of from about 0.05 mm to about 3 mm, more preferably from about 0.15 mm to about 2 mm, still more preferably from about 0.2 mm to about 1 mm.

It is also preferred in the present invention that the mesh is composed by a material having certain hardness. Preferably, the mesh is composed by a material which is harder than the fibers to be assessed. Such materials useful herein include, for example, metals such as steel and iron, and hard plastics which are not extended when contacted by fibers to be assessed. When the mesh is composed by softer materials than the fibers to be assessed, the mesh tends to be easy to extend while pressed by the fibers. Thus, it may become difficult for the fibers, i.e., any fibers regardless its condition, to pass through the mesh hole, and it may also becomes difficult to assess conditions appropriately.

Meshes may also have a different color to the sample of fibers. Particularly, when the assessment contains visual inspection and/or picture analysis, it may be preferred meshes to have a color contrasting with the fibers. For example, if dark hair fiber sample is provided, then it is preferred to provide light-colored mesh, e.g. white or beige. Mesh may also be capable of being distinguished from fibers under conditions alternative to daylight conditions, such as in the absence of any light (e.g. fluorescent and/or phosphorescent) and/or under infra-red light.

Treatment

The method may also comprise the step of treating the sample (so-called "treatment step"). The treatment step may be carried out before the sample provision step. The treatment step can be carried out before or after the sample provision step, and is preferably carried out before the measuring step. The treatment step may be carried out by treating the sample using any suitable cosmetic composition, chemical and/or mechanical treatment.

This step may be carried out by applying a cosmetic composition onto keratin fiber. Any suitable cosmetic composition known in the art may be used such as shampoos, conditioning compositions, hair rinse-off treatments, hair leave-on treatments, styling compositions. For example, any commercially available shampoos, conditioners, hair rinse-off treatments and hair leave-on treatments of tradename Pantene® and Head & Shoulders® may be used.

Only one composition may be applied onto fibers. Alternatively, two or several compositions may be applied simultaneously or sequentially. In addition, before and/or after applying each composition, the fibers may further be wetted, rinsed and/or dried. In one embodiment, the treating step comprises treating (washing) the fibers with a shampoo, then rinsing the washed fibers with water, then drying the fibers. In another embodiment, the treating step comprises treating (washing) the fibers with a shampoo, then rinsing the washed fibers with water, then treating the fibers with a conditioning composition, then rinsing the treated fibers with water, then drying the fibers. In another embodiment, the treating step comprises treating (washing) the fibers with a shampoo, then rinsing the washed fibers with water, then treating the fibers with a conditioning composition, then rinsing the treated fibers with water, then treating at least one time the fibers with a hair rinse-off treatment, then rinsing the treated fibers with water, then drying the fibers.

Alternatively or complementary, this step may be carried out by chemically treating the fibers using a chemical treatment. Any suitable chemical treatment known in the art may be used such as permanent waving treatment, bleaching treatment and/or color-dyeing treatment.

Alternatively or complementary, this step may be carried out by mechanically treating the fibers. Any suitable mechanical treatment known in the art may be used such as brushing, combing, towel rubbing, and/or blow drying.

Contacting

The method also comprises the step of placing said sample of fibers in contact with the mesh and allowing the fibers to pass through the mesh holes (so-called "contacting step").

Preferably, the mesh contacts the sample from fiber tip side of the sample, so that the mesh face can contact the sample substantially vertically (to fiber length).

Alternatively, the mesh may contact from the side direction of the fiber sample, when assessing fiber frizz and/or alignment.

Quantity Measurement

The method also comprises the step of measuring the quantity of fibers passing through the mesh, of the sample (so-called "quantity measuring step").

Preferably, the quantity of fibers passing through the mesh is assessed by direct visual inspection and/or by picture analysis. Direct visual inspection comprises the step of looking at the sample, without needing any electrical measuring device. Picture analysis comprises the step of taking pictures of the or each sample of at least one fiber or substrate, optionally treating and/or modifying pictures such as increasing the contrast between the fibers or substrates and the particles, and analyzing the pictures by visual inspection or via a computer-aided inspection.

The direct visual inspection or the picture analysis may be conducted by the skilled person and/or by the non-skilled person, including the consumer and/or the end-user. When the inspection is conducted by a non-skilled person, this person may not need to be trained before the inspection as the assessment of the condition of fibers, derived to the assessment of the quantity of fibers passing through the mesh, is easily understandable.

Alternatively, the quantity of fibers passing through the mesh may be assessed by measuring the weight of the fiber portion passing through the mesh. For example, such fiber portions are cut while passing through the mesh, before measuring the weight.

Condition Assessment

The condition to assess can be selected from the group consisting of fiber breakage, split-end, fiber frizz, fiber alignment, fiber strength, and mixtures thereof. Such conditions can be interpreted into fiber damage. When the fiber is keratin fibers, such conditions can be interpreted into keratin fiber healthiness.

For example, fiber breakage, split-end and strength can be assessed by the quantity measurement when contacting mesh from the tip end of the fiber samples. When a larger quantity of fibers of the sample passes through the mesh holes, it is assessed that the sample has less breakage, less split-end and/or more strength.

Fiber frizz and alignment can be also assessed by the quantity measurement when contacting the mesh from tip end of the fiber samples. When a larger quantity of fibers of the sample pass through the mesh holes, are it is assessed that the sample has less frizz and/or more alignment.

Alternatively, fiber frizz and alignment may be assessed by the quantity measurement when contacting the mesh from the side direction of the fiber sample. In this assessment, in contrast to the above similar frizz/alignment assessment when contacting the mesh from the tip end of the fiber sample, the sample is assessed to have more frizz and/or less alignment, when a larger quantity of fibers of the sample pass through the mesh holes.

Comparison

The method may also comprise the step of quantity of different samples (so-called "comparison step").

In one embodiment, one sample may comprise the tip portion of fibers and the other sample may comprise the root portion of the same fibers. Providing and comparing different portions of the same fibers, particularly tip versus root, allows assessing the difference of the degree of damages over time, as the fibers grow.

The comparison step is also beneficial for comparing the effects of one treatment onto fibers versus no treatment. In one embodiment, one sample may comprise untreated fibers and the other sample comprises fibers treated with a cosmetic composition. The other sample may be treated with a shampoo, and/or a conditioning composition, and/or a hair rinse-off treatment, and/or a leave-on treatment, and/or any other suitable cosmetic composition. Comparing treated fiber(s) and untreated fiber(s) is beneficial for assessing the damaging effects of the compositions such as shampoos onto hair or, in contrast, for assessing the benefits of the compositions such as conditioning compositions for preventing and/or repairing the damages of the fiber(s).

The comparison step is further beneficial for comparing the efficacy of at least two different treatments for preventing and/or repairing the damages of fibers. In one embodiment, the samples may be treated with different cosmetic compositions. For example and non-exhaustively, (1) one sample may be treated with one shampoo and the other sample with another shampoo; (2) one sample may be treated with one shampoo and the other sample may be treated with the same shampoo and then one conditioner; (3) one sample may be treated with one shampoo and then one conditioner and the other sample may be treated with the same shampoo and then another conditioner, (4) one sample may be treated with one shampoo and then one conditioner and the other sample may be treated with the same shampoo, then the same conditioner, and then a rinse-off treatment, (5) one sample may be treated with one shampoo and then one conditioner and the other sample may be treated with the same shampoo, then the same conditioner, and then a leave-on treatment, (6) one sample may be treated with one shampoo and then one conditioner and the other sample may be treated with another shampoo and then the same conditioner; (7) one sample may be treated one time with one shampoo and the other sample may be treated two or several time with the same shampoo; (8) one sample may be treated one time with one conditioner and the other sample may be treated two or several times with the same conditioner. Comparing differently treated fiber(s) is beneficial for comparing the damaging effects of different shampoos (see (1)); for assessing the mitigating effects of conditioners onto shampoo treatments (see (2)); for comparing the benefits of conditioning compositions for preventing and/or repairing the damages of the fiber(s) (see (3)); for assessing the mitigating effects of rinse-off treatments onto shampoo treatments (see (4)); for assessing the mitigating effects of leave-on treatments onto shampoo treatments (see (5)); for comparing the mitigating effects of one conditioners onto different shampoo treatments (see (6)); for comparing the effects of repeating treatments onto fiber(s) (see (7) and (8)).

The comparison step is beneficial for example for comparing the effects of chemical and/or mechanical treatments. For example, in one embodiment, one sample may comprise untreated fiber(s) and the other sample comprises fibers being chemically-treated. Alternatively, the samples may comprise fiber(s) be treated with different chemical treatments. In another embodiment, one sample may comprise untreated fiber(s) and the other sample comprises fibers being mechanically-treated. Alternatively, the samples may comprise fiber(s) be treated with different mechanical treatments.

Advertisement Support

The method may also comprise the step of utilizing said assessment to support advertising claims (so-called "advertising step"). Making advertising steps based on the outcome of the comparison between two different samples is beneficial for example for advertising the efficacy of a treatment for preventing and/or repairing damages to fibers and/or for advertising the superiority of one treatment versus another treatment for preventing and/or repairing damages. When advertising one treatment (e.g. a conditioning composition) versus another one, the data and/or the pictures obtained using this method may be used therefore support and/or demonstrate advertising claims according to which said treatment provide higher performance versus the other one for preventing and/or repairing fiber damages.

EXAMPLE

Materials

Sample: 15 cm long, a bundle of about 2 g hair fibers (about 2,000 hair fibers) of Oriental non-colored/non-permed hair Mesh: made of stainless-steel and with holes having a size of approximately 0.7 mm Non-conditioning shampoo composition: having pH=5-7 and comprising Ammonium laureth-3 sulfate (12.8%), Ammonium lauryl sulfate (9.1%), Cocamide DEA (2.3%), Ammonium xylenesulfonate (1%), EDTA (0.1%), Preservatives (<1%), Water q.s. to 100%.

Conditioning shampoo composition: having pH=5-7, and comprising Sodium laureth-3 sulfate (6.0%), Sodium lauryl sulfate (6.0%), Cocamidopropyl betaine (1%), Cocamide MEA (0.85%), Glycol Disterate (1.5%), Guar Hydroxypropyltrimonium Chloride (0.3%), Polyquaternium-76 (0.1%), Dimethicone (2%), Preservatives (0.6%), Water q.s. to 100%.

Conditioning composition: having pH=5-7, and comprising Behentrimonium methosulfate (1.8%), Fatty alcohols (5.2%), Aminodimethicone (2.5%), Preservatives (0.6%), Water q.s. to 100%.

Percentages of compounds are weight percent per total weight of the composition

Protocol

Depending on the method carried out, some of the steps may be omitted, e.g. the treating step.

1. [Sample provision step] Preparing the above hair sample.
2. [Mesh provision step] Preparing the above mesh.
3. [Treatment step A] In this Treatment step A, the samples are cosmetically treated by applying Non-conditioning shampoo composition, and also mechanically treated by combing, as described below:
   3.1 Hang a sample on bar
   3.2 Wet the sample 20 seconds and squeeze the sample to remove excess water
   3.3 Apply Non-conditioning shampoo composition 0.2 ml the sample and milk for 30 seconds 3.4 Rinse the sample for 30 seconds and squeeze the sample to remove excess water
3.5 Leave the sample in the control humidity and temperature (Humidity 45%, Temperature 21° C.) for one night.
3.6 Combing the sample 8000 times
3.7 Repeat 3.1-3.6 protocol
3.8 Repeat 3.1-3.5 protocol
4. [Treatment step B] In this Treatment step B, the samples are cosmetically treated by applying Non-conditioning shampoo composition, Conditioning shampoo composition and Conditioning composition, and also mechanically treated by combing, as described below.
4.1 Hang a sample on bar
4.2 Wet the sample 20 seconds and squeeze the sample to remove excess water
4.3 Apply Conditioning shampoo composition 0.2 ml the sample and milk for 30 seconds
4.4 Rinse the sample for 30 seconds and squeeze the sample to remove excess water
4.5 Apply Conditioning composition 0.2ml the sample and milk for 30seconds
4.6 Rinse the sample for 30 seconds and squeeze the sample to remove excess water
4.7 Leave the sample in the control humidity and temperature (Humidity 45%, Temperature 21° C.) for one night.
4.8 Combing the sample 8000 times
4.9 Repeat 4.1-4.8 protocol
4.10 Repeat 4.1-4.7 protocol
5. [Contacting step] Put the banding band at 3 cm from hair tip of each sample, and hold each sample so that its hair tip faces upward and at a same height, and contacting mesh from the upward (from the hair tip side) approximately vertically to the length of hair
6. [Measuring step] Measuring the quantity of hair fibers passing through the mesh by direct visual inspection.
7. [Condition assessment step] Assessing fiber damage condition based on the quantity of the fibers.

Assessment and Comparison of Damages of Hair Fiber Tip Portions That Are Differently-Treated According to the above materials and protocols, two samples are provided with different treatments as shown in Table 1, and hair damages are assessed. The assessment results are shown below in Table 1.

TABLE 1

| Samples | Treatment | Quantity of fibers passing through the mesh holes | Assessment of hair damages |
| --- | --- | --- | --- |
| A | Treatment step A | Less amount of fibers, as shown at the left side of FIG. 1 | More damaged |
| B | Treatment step B | More amount of fibers, as shown at the right side of FIG. 1 | Less damaged |

As shown in Table 1, the damage of Sample B is much lower than that of Sample A. This also shows the efficacy of Conditioning shampoo composition and Conditioning composition, which were used in only Treatment step B for Sample B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessing a condition of fibers comprising the steps of:
    providing at least one sample of fibers wherein the fibers have a length of 1 cm to 50 cm;
    providing a mesh, wherein the mesh has holes which at least one fiber pass through wherein the hole of the mesh has a size of from 1.1 times to 20 times larger than the diameter of the fiber;
    placing said sample of fibers in contact with the mesh and allowing the fibers to pass through the mesh holes; and,
    measuring the quantity of fibers passing through the mesh, of the sample;
    assessing a condition of the sample based on the quantity of fibers wherein the fibers are keratin fiber wherein the condition to assess is selected from the group consisting of fiber breakage, split-end, fiber frizz, fiber alignment, fiber strength, and mixtures thereof, fiber healthiness, fiber damage, and mixtures thereof.

2. The method, according to claim 1, wherein the keratin fiber is human hair.

3. The method of claim 1, wherein a selected portion of the sample of fibers is an end tip of the sample.

4. The method of claim 1, wherein the quantity is measured by direct visual inspection.

5. A method for assessing and comparing damages of different fibers comprising the steps of:
    providing at least two different samples of fibers wherein the fibers have a length of 1 cm to 50 cm;
    providing at least one mesh, wherein the mesh has holes which at least one fiber pass through wherein the hole of the mesh has a size of from 1.1 times to 20 times larger than the diameter of the fiber;
    placing said samples of fibers in contact with the mesh and allowing the fibers to pass through the mesh holes; and,
    measuring the quantity of fibers passing through the mesh, of the samples;
    assessing conditions of the samples based on the quantity of fibers wherein the condition to assess is selected from the group consisting of fiber breakage, split-end, fiber frizz, fiber alignment, fiber strength, and mixtures thereof, fiber healthiness, fiber damage, and mixtures thereof;
    comparing the condition of the samples wherein the fibers are keratin fiber.

6. The method of claim 5, wherein the samples differ from each other by the origin of the fibers, the portion of the fibers and/or the treatment(s) applied to the fibers.

7. The method of claim 5, wherein one sample comprises untreated fiber(s) and the other sample comprises fiber(s) treated with a cosmetic, chemical and/or mechanical treatment.

8. The method of claim 5, wherein the samples are treated with different cosmetic, chemical, and/or mechanical treatments.

9. The method of claim 7 or claim 8, further comprising the step of utilizing said comparison to support advertising claims about the efficacy of a treatment.

* * * * *